(12) United States Patent
Gschneidner

(10) Patent No.: US 7,217,703 B2
(45) Date of Patent: May 15, 2007

(54) 8-(2-HYDROXYPHENOXY)-OCTYLDIETHANOLAMINE AND SALTS THEREOF FOR DELIVERY OF ACTIVE AGENTS

(75) Inventor: David Gschneidner, Thornwood, NY (US)

(73) Assignee: Emisphere Technologies, Inc., Tarrytown, NY (US)

( * ) Notice: Subject to any disclaimer, the term of this patent is extended or adjusted under 35 U.S.C. 154(b) by 17 days.

(21) Appl. No.: 11/109,046

(22) Filed: Apr. 18, 2005

(65) Prior Publication Data

US 2005/0277621 A1 Dec. 15, 2005

Related U.S. Application Data

(60) Provisional application No. 60/575,320, filed on May 28, 2004, provisional application No. 60/563,281, filed on Apr. 16, 2004.

(51) Int. Cl.
*A61K 31/66* (2006.01)
*A61K 31/138* (2006.01)
*C07C 215/10* (2006.01)

(52) U.S. Cl. ............ 514/102; 514/651; 564/347; 564/348

(58) Field of Classification Search ........ 514/652, 514/651, 102; 564/349, 347, 348
See application file for complete search history.

(56) References Cited

U.S. PATENT DOCUMENTS

| 5,401,516 A | 3/1995 | Milstein et al. |
| 5,443,841 A | 8/1995 | Milstein et al. |
| 5,629,020 A | 5/1997 | Leone-Bay et al. |
| 5,643,957 A | 7/1997 | Leone-Bay et al. |
| 5,766,633 A | 6/1998 | Milstein et al. |
| RE35,862 E | 7/1998 | Steiner et al. |
| 5,776,888 A | 7/1998 | Leone-Bay et al. |
| 5,866,536 A | 2/1999 | Leone-Bay et al. |

FOREIGN PATENT DOCUMENTS

| WO | WO 00/40203 | 7/2000 |
| WO | WO 00/50386 | 8/2000 |
| WO | WO 00/59863 | 10/2000 |
| WO | WO 01/32130 | 5/2001 |
| WO | WO 01/32596 | 5/2001 |
| WO | WO/03/045306 | 6/2003 |
| WO | WO 03/045306 | 6/2003 |
| WO | WO 03/045331 | 6/2003 |

OTHER PUBLICATIONS

Brown, et al., "The role of bisphosphonates in breast and prostate cancers", Endocrine-Related Cancer, vol. 11: pp. 207-224*(2004).
P. Major, "The Use of Zoledronic Acid, a Novel, Highly Potent Bisphosphonate, for the Treatment of the Hypercalcemia of Malignancy", The Oncologist, vol. 7: pp. 481-491*(2002).
Tripathy, et al., "Oral ibandronate for the treatment of metastatic bone disease in breast cancer: efficacy and safety results from a randomized, double-blind, placebo-controlled trial", Annals of Oncology, vol. 15: pp. 743-750 (Jan. 2004).
R. Coleman, "Management of Bone Metastases", The Oncologist, vol. 5: pp. 463-470 (Sep. 2000).
Boissier, et al., "Bisphosphonates Inhibit Breast and Prostate Carcinoma Cell Invasion, an Early Event in the Formation of Bone Metastates", Cancer Research, vol. 60: pp. 2949-2954 (Jun. 2000).
E. Jantunen, "Bisphosphonate therapy in multiple myeloma: past, present, future", European Journal of Haematology, vol. 9: pp. 257-264 (2002).

*Primary Examiner*—Rosalynd Keys
(74) *Attorney, Agent, or Firm*—Darby & Darby

(57) ABSTRACT

The present invention provides 8-(2-hydroxyphenoxy)octyldiethanolamine) and salts thereof, compositions containing the same and one or more active agents, and methods of administering active agents with the same. The delivery agents of the present invention are well suited for forming non-covalent mixtures with active agents for oral, intracolonic, pulmonary, and other routes of administration to animals.

24 Claims, 2 Drawing Sheets

8-(2-HYDROXYPHENOXY)-OCTYLDIETHANOLAMINE AND SALTS THEREOF FOR DELIVERY OF ACTIVE AGENTS

This application claims the benefit of U.S. Provisional Application No. 60/575,320, filed May 28, 2004 and U.S. Provisional Application No. 60/563,281, filed Apr. 16, 2004. Each of these applications are hereby incorporated by reference.

FIELD OF THE INVENTION

The present invention provides 8-(2-hydroxyphenoxy) octyldiethanolamine and salts thereof, compositions containing the same and one or more active agents, and methods of administering active agents with the same. The delivery agents of the present invention are well suited for forming non-covalent mixtures with active agents for oral, intracolonic, pulmonary, and other routes of administration to animals.

BACKGROUND OF THE INVENTION

Conventional means for delivering active agents are often severely limited by biological, chemical, and physical barriers. Typically, these barriers are imposed by the environment through which delivery occurs, the environment of the target for delivery, and/or the target itself. Biologically and chemically active agents are particularly vulnerable to such barriers.

In the delivery to animals of biologically active and chemically active pharmacological and therapeutic agents, barriers are imposed by the body. Examples of physical barriers are the skin, lipid bi-layers and various organ membranes that are relatively impermeable to certain active agents but must be traversed before reaching a target, such as the circulatory system. Chemical barriers include, but are not limited to, pH variations in the gastrointestinal (GI) tract and degrading enzymes.

These barriers are of particular significance in the design of oral delivery systems. Oral delivery of many biologically or chemically active agents would be the route of choice for administration to animals if not for biological, chemical, and physical barriers. Among the numerous agents which are not typically amenable to oral administration are biologically or chemically active peptides, such as calcitonin and insulin; polysaccharides, and in particular mucopolysaccharides including, but not limited to, heparin; heparinoids; antibiotics; and other organic substances. These agents may be rapidly rendered ineffective or destroyed in the gastrointestinal tract by acid hydrolysis, enzymes, and the like. In addition, the size and structure of macromolecular drugs may prohibit absorption.

Earlier methods for orally administering vulnerable pharmacological agents have relied on the co-administration of adjuvants (e.g., resorcinols and non-ionic surfactants such as polyoxyethylene oleyl ether and n-hexadecylpolyethylene ether) to increase artificially the permeability of the intestinal walls, as well as the co-administration of enzymatic inhibitors (e.g., pancreatic trypsin inhibitors, diisopropylfluorophosphate (DFF) and trasylol) to inhibit enzymatic degradation. Liposomes have also been described as drug delivery systems for insulin and heparin. However, broad spectrum use of such drug delivery systems is precluded because: (1) the systems require toxic amounts of adjuvants or inhibitors; (2) suitable low molecular weight cargos, i.e. active agents, are not available; (3) the systems exhibit poor stability and inadequate shelf life; (4) the systems are difficult to manufacture; (5) the systems fail to protect the active agent (cargo); (6) the systems adversely alter the active agent; or (7) the systems fail to allow or promote absorption of the active agent.

Proteinoid microspheres have been used to deliver pharmaceuticals. See, for example, U.S. Pat. Nos. 5,401,516; 5,443,841; and Re. 35,862. In addition, certain modified amino acids have been used to deliver pharmaceuticals. See, for example, U.S. Pat. Nos. 5,629,020; 5,643,957; 5,766,633; 5,776,888; and 5,866,536.

More recently, a polymer has been conjugated to a modified amino acid or a derivative thereof via a linkage group to provide for polymeric delivery agents. The modified polymer may be any polymer, but preferred polymers include, but are not limited to, polyethylene glycol (PEG), and derivatives thereof. See, for example, International Patent Publication No. WO 00/40203.

International Patent Publication Nos. WO 01/32130 and WO 01/32596 disclose particular phenyl amine carboxylic acid compounds and phenoxy carboxylic acid compounds for delivering active agents. International Publication No. WO 00/50386 also discloses amine delivery agents.

International Application No. PCT/US02/36552, filed Nov. 13, 2002, published as International Application No. WO 03/045306, and its priority applications, namely U.S. Provisional Application No. 60/350,488, filed Nov. 13, 2001, and U.S. Provisional Application No. 60/357,288, filed Feb. 15, 2002, disclose phenoxy amine compounds and compositions for delivering active agents. Each of the above applications are hereby incorporated by reference.

Recently, some articles have discussed the use of certain bisphosphonates for treating various malignant diseases. See, e.g., Brown, et al., *Endocr. Relat. Cancer*, 2004 11(2): 207–24); *Major Oncologist*, 2002 7:481–491; Tripathy et al., *Ann. Oncol.* 2004 (5): 743–50;Coleman, *Oncologist*, 2000 5:463–470; Boissier, et al., *Cancer Res.*, 2000 60:2949–2954; and Jantunen, *Eur J Haematol.* 2002 69(5–6):257–64, all of which are incorporated herein by reference.

However, there is still a need for simple, inexpensive delivery systems which are easily prepared and which can deliver a broad range of active agents by various routes.

SUMMARY OF THE INVENTION

The present invention provides compounds and compositions which facilitate the delivery of active agents. Delivery agent compounds of the present invention include those having the following formula:

Compound 1

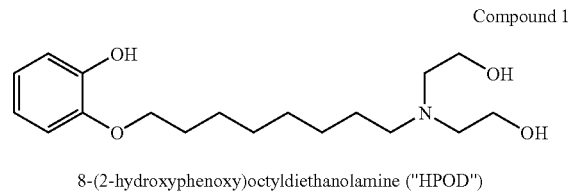

8-(2-hydroxyphenoxy)octyldiethanolamine ("HPOD")

and salts thereof. A preferred delivery agent compound is the mesylate salt of compound 1.

Mixtures of these delivery agent compounds may also be used.

The invention also provides a composition, such as a pharmaceutical composition, comprising at least one of the delivery agent compounds of the formula above, and at least one active agent. These compositions deliver active agents to selected biological systems in increased or improved bioavailability of the active agent compared to administration of the active agent without the delivery agent compound.

Also provided are dosage unit forms comprising the compositions. The dosage unit may be in the form of a liquid or a solid, such as a tablet, capsule or particle, including a powder or sachet.

Another embodiment is a method for administering an active agent to an animal, particularly an animal in need of the active agent, by administering a composition comprising at least one of the agent compounds above and the active agent to the animal. Preferred routes of administration include the oral and intracolonic routes.

Yet another embodiment is a method of treating a disease or for achieving a desired physiological effect in an animal in need thereof by administering an effective amount of the composition of the present invention.

Yet another embodiment is a method of preparing a composition of the present invention by mixing at least one delivery agent compound of the formula above, and at least one active agent. Mixtures of active agents may also be used with HPOD.

Yet another embodiment is a method of treating osteoporosis and/or Paget's disease in an animal (e.g., a person or other mammal) in need thereof by administering an effective amount of a pharmaceutical composition comprising a delivery agent compound of the present invention and a bisphosphonate. A preferred delivery agent of the present invention is the mesylate salt of compound I. Preferred bisphosphonates, include, but are not limited to, alendronate, clodronate, etidronate, ibandronate, incadronate, minodronate, neridronate, olpadronate, pamidronate, risedronate, tiludronate, zoledronate, EB1053, and YH529. A more preferred bisphosphonate is ibandronate.

Still another embodiment is a method of inhibiting osteoclasts in an animal (e.g., a person or other mammal) in need thereof by administering an effective amount of a pharmaceutical composition comprising a delivery agent compound of the present invention and a bisphosphonate. A preferred delivery agent of the present invention is the mesylate salt of compound I. Preferred bisphosphonates, include, but are not limited to, alendronate, clodronate, etidronate, ibandronate, incadronate, minodronate, neridronate, olpadronate, pamidronate, risedronate, tiludronate, zoledronate, EB1053, and YH529. A more preferred bisphosphonate is ibandronate.

Still another embodiment is a method for treating a malignant disease in an animal (e.g., a person or other mammal) in need thereof by administering an effective amount of a pharmaceutical composition comprising (a) at least one compound selected from 8-(2-hydroxyphenoxy) octyldiethanolamine and salts thereof, and (b) one or more bisphosphonates. The malignant disease is preferably selected from breast cancer, prostate cancer, testicular cancer, colon cancer, pancreatic cancer, endometrial cancer, small cell and non-small cell cancer of the lung, ovarian cancer, cervical cancer, myeloid leukemia, lymphocyltic leukemia, lymphoma, hepatic tumors, medullary thyroid carcinoma, multiple myeloma, and melanoma retinoblastoma, and sarcomas of the soft tissue and bone, i.e. neoplasms that express vitamin D receptors. According to one embodiment, the bisphosphonate is ibandronate.

Still another embodiment is a method for treating hypercalcemia of malignancy in an animal (e.g., a person or other mammal) in need thereof by administering an effective amount of a pharmaceutical composition comprising (a) at least one compound selected from 8-(2-hydroxyphenoxy) octyldiethanolamine and salts thereof, and (b) one more bisphosphonates. According to one embodiment, the bisphosphonate is ibandronate.

Still another embodiment is a method for treating osteolytic bone mestastases in an animal (e.g., a person or other mammal) in need thereof by administering an effective amount of a pharmaceutical composition comprising (a) at least one compound selected from 8-(2-hydroxyphenoxy) octyldiethanolamine and salts thereof, and (b) one more bisphosphonates.

DETAILED DESCRIPTION OF THE INVENTION

Definitions

Figure 1:
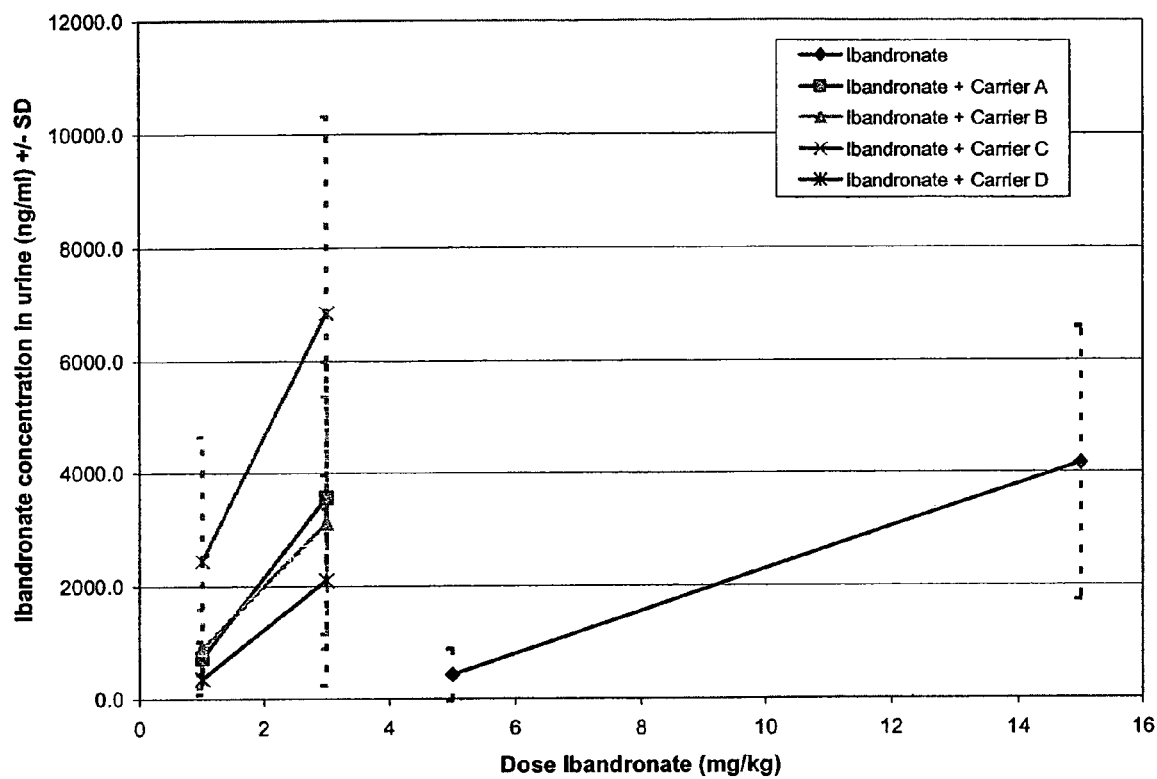
FIG. 1 depicts the mean urine Ibandronate concentration following administration of Ibandronate alone (-♦-) or with any one of four delivery agents (SNAC (-■-), FSAA (-▲-), HPOD mesylate (-x-), and SNAD (-*-)).

The term "HPOD" as used herein (unless otherwise indicated) refers to 8-(2-hydroxyphenoxy)octyldiethanolamine and salts thereof.

The term "delivery agent" as used herein refers to phenoxy amine compounds of the present invention, including crystalline polymorphic forms thereof.

An "effective amount of drug" is an amount of the active agent (e.g., heparin) which is effective to treat or prevent a condition in a living organism to whom it is administered over some period of time, e.g., provides a therapeutic effect during a desired dosing interval. Effective doses will vary, as recognized by those skilled in the art, depending on the route of administration, excipient usage, and the possibility of co-usage with other agents for treating a condition.

The term "treat", "treating", or "treated" refers to administering an active agent with the purpose to cure, heal, alleviate, relieve, alter, remedy, ameliorate, improve, or affect a condition (e.g., a disease), the symptoms of the condition, or the predisposition toward the condition.

An "effective amount of delivery agent" is an amount of the delivery agent which promotes the absorption of a desired amount of the active agent via any route of administration (such as those discussed in this application including, but not limited to, the oral (e.g., across a biological membrane in the gastrointestinal tract), nasal, pulmonary, dermal, vaginal, and/or ocular route).

As used herein, the term "about" means within 10% of a given value, preferably within 5%, and more preferably within 1% of a given value. Alternatively, the term "about" means that a value can fall within a scientifically acceptable error range for that type of value, which will depend on how qualitative a measurement can be given the available tools.

Delivery Agent Compounds

The delivery agent compounds may be in the form of the free base or salts thereof. Suitable salts include, but are not limited to, organic and inorganic salts, for example ammonium, acetate salt, citrate salt, halide (preferably hydrochloride), hydroxide, sulfate, nitrate, phosphate, alkoxy, perchlorate, tetrafluoroborate, carboxylate, mesylate, fumerate, malonate, succinate, tartrate, acetate, gluconate, and maleate. Preferred salts include, but are not limited to, citrate and mesylate salts. The salts may also be solvates, including ethanol solvates, and hydrates.

Salts of the delivery agent compounds of the present invention may be prepared by methods known in the art. For example, citrate salts and mesylate salts may be prepared in ethanol, toluene and citric acid.

The delivery agent compound may be purified by recrystallization or by fractionation on one or more solid chromatographic supports, alone or linked in tandem. Suitable recrystallization solvent systems include, but are not limited to, ethanol, water, heptane, ethyl acetate, acetonitrile, acetone, methanol, and tetrahydrofuran (THF) and mixtures thereof. Fractionation may be performed on a suitable chromatographic support such as alumina, using methanol/n-propanol mixtures as the mobile phase; reverse phase chromatography using trifluoroacetic acid/acetonitrile mixtures as the mobile phase; and ion exchange chromatography using water or an appropriate buffer as the mobile phase. When anion exchange chromatography is performed, preferably a 0–500 mM sodium chloride gradient is employed.

The delivery agent may contain a polymer conjugated to it, e.g., as described in International Publication No. WO 03/045331, which is incorporated herein by reference. For example, the delivery agent may contain a polymer conjugated to it by a linkage group selected from —NHC(O)NH—, —C(O)NH—, —NHC(O), —OOC—, —COO—, —NHC(O)O—, —OC(O)NH—, —CH$_2$NH —NHCH$_2$—, —CH$_2$NHC(O)O—, —OC(O)NHCH$_2$—, —CH$_2$NHCOCH$_2$O—, —OCH$_2$C(O)NHCH$_2$—, —NHC(O)CH$_2$O—, —OCH$_2$C(O)NH—, —NH—, —O—, and carbon-carbon bond, with the proviso that the polymeric delivery agent is not a polypeptide or polyamino acid. The polymer may be any polymer including, but not limited to, alternating copolymers, block copolymers and random copolymers, which are safe for use in mammals. Preferred polymers include, but are not limited to, polyethylene; polyacrylates; polymethacrylates; poly(oxyethylene); poly (propylene); polypropylene glycol; polyethylene glycol (PEG); and derivatives thereof and combinations thereof. The molecular weight of the polymer typically ranges from about 100 to about 200,000 daltons. The molecular weight of the polymer preferably ranges from about 200 to about 10,000 daltons. In one embodiment, the molecular weight of the polymer ranges from about 200 to about 600 daltons and more preferably ranges from about 300 to about 550 daltons.

Active Agents

Active agents suitable for use in the present invention include biologically active agents and chemically active agents, including, but not limited to, pesticides, pharmacological agents, and therapeutic agents. Suitable active agents include those that are rendered less effective, ineffective or are destroyed in the gastro-intestinal tract by acid hydrolysis, enzymes and the like. Also included as suitable active agents are those macromolecular agents whose physiochemical characteristics, such as, size, structure or charge, prohibit or impede absorption when dosed orally.

For example, biologically or chemically active agents suitable for use in the present invention include, but are not limited to, proteins; polypeptides; peptides; hormones; polysaccharides, and particularly mixtures of muco-polysaccharides; carbohydrates; lipids; small polar organic molecules (i.e. polar organic molecules having a molecular weight of 500 daltons or less); other organic compounds; and particularly compounds which by themselves do not pass (or which pass only a fraction of the administered dose) through the gastro-intestinal mucosa and/or are susceptible to chemical cleavage by acids and enzymes in the gastro-intestinal tract; or any combination thereof.

Further examples include, but are not limited to, the following, including synthetic, natural or recombinant sources thereof: growth hormones, including human growth hormones (hGH), recombinant human growth hormones (rhGH), bovine growth hormones, and porcine growth hormones; growth hormone releasing hormones; growth hormone releasing factor, interferons, including α (e.g., interferon alfacon-1 (available as Infergen® from InterMune, Inc. of Brisbane, Calif.)), β and γ; interleukin-1; interleukin-2; insulin, including porcine, bovine, human, and human recombinant, optionally having counter ions including zinc, sodium, calcium and ammonium; insulin-like growth factor, including IGF-1; heparin, including unfractionated heparin, heparinoids, dermatans, chondroitins, low molecular weight heparin, very low molecular weight heparin and ultra low molecular weight heparin; calcitonin, including salmon, eel, porcine and human; erythropoietin; atrial naturetic factor; antigens; monoclonal antibodies; somatostatin; protease inhibitors; adrenocorticotropin, gonadotropin releasing hormone; oxytocin; leutinizing-hormone-releasing-hormone; follicle stimulating hormone; glucocerebrosidase; thrombopoietin; filgrastim; prostaglandins; cyclosporin; vasopressin; cromolyn sodium (sodium or disodium chromoglycate); vancomycin; desferrioxamine (DFO); parathyroid hormone (PTH), including its fragments; anti-migraine agents such as BIBN-4096BS and other calcitonin gene-related proteins antagonists; glucagon-like peptide 1 (GLP-1); antimicrobials, including antibiotics, anti-bacterials and anti-fungal agents; vitamins; analogs, fragments, mimetics or polyethylene glycol (PEG)-modified derivatives of these compounds; or any combination thereof. Non-limiting examples of antibiotics include gram-positive acting, bacteriocidal, lipopeptidal and cyclic peptidal antibiotics, such as daptomycin and analogs thereof.

Additional active agents include amylin and amylin antagonist, as well as peptide PYY and peptide PYY agonists including, but limited to peptide PYY [3–36].

Active agents of the present invention further include bisphosphonates. Bisphosphonates of the present invention include, but are not limited to, alendronate, clodronate, etidronate, ibandronate, incadronate, minodronate, neridronate, olpadronate, pamidronate, risedronate, tiludronate, zoledronate, EB1053, and YH529.

Delivery Systems

The composition of the present invention comprises one or more delivery agent compounds of the present invention, and one or more active agents. In one embodiment, one or more of the delivery agent compounds, or salts of these compounds, or poly amino acids or peptides of which these compounds or salts form one or more of the units thereof, may be used as a delivery agent by mixing with the active agent prior to administration to form an administration composition.

The administration compositions may be in the form of a liquid. The solution medium may be water (for example, for salmon calcitonin, parathyroid hormone, and erythropoietin), 25% aqueous propylene glycol (for example, for heparin) and phosphate buffer (for example, for rhGH).

Other dosing vehicles include polyethylene glycol. Dosing solutions may be prepared by mixing a solution of the delivery agent compound with a solution of the active agent, just prior to administration. Alternately, a solution of the delivery agent compound (or active agent) may be mixed with the solid form of the active agent (or delivery agent compound). The delivery agent compound and the active agent may also be mixed as dry powders. The delivery agent compound and the active agent can also be admixed during the manufacturing process.

The dosing solutions may optionally contain additives such as phosphate buffer salts, citric acid, glycols, or other dispersing agents. Stabilizing additives may be incorporated into the solution, preferably at a concentration ranging between about 0.1 and 20% (w/v).

The administration compositions may alternately be in the form of a solid, such as a tablet, capsule or particle, such as a powder or sachet. Solid dosage forms may be prepared by mixing the solid form of the compound with the solid form of the active agent. Alternately, a solid may be obtained from a solution of compound and active agent by methods known in the art, such as freeze-drying (lyophilization), precipitation, crystallization and solid dispersion.

The administration compositions of the present invention may also include one or more enzyme inhibitors. Such enzyme inhibitors include, but are not limited to, compounds such as actinonin or epiactinonin and derivatives thereof. Other enzyme inhibitors include, but are not limited to, aprotinin (Trasylol) and Bowman-Birk inhibitor.

The amount of active agent used in an administration composition of the present invention is an amount effective to accomplish the purpose of the particular active agent for the target indication. The amount of active agent in the compositions typically is a pharmacologically, biologically, therapeutically, or chemically effective amount. However, the amount can be less than that amount when the composition is used in a dosage unit form because the dosage unit form may contain a plurality of delivery agent compound/active agent compositions or may contain a divided pharmacologically, biologically, therapeutically, or chemically effective amount. The total effective amount can then be administered in cumulative units containing, in total, an effective amount of the active agent.

The total amount of active agent to be used can be determined by methods known to those skilled in the art. However, because the compositions of the invention may deliver active agents more efficiently than compositions containing the active agent alone, lower amounts of biologically or chemically active agents than those used in prior dosage unit forms or delivery systems can be administered to the subject, while still achieving the same blood levels and/or therapeutic effects.

The presently disclosed delivery agent compounds facilitate the delivery of biologically and chemically active agents, particularly in oral, intranasal, sublingual, intraduodenal, subcutaneous, buccal, intracolonic, rectal, vaginal, mucosal, pulmonary, transdermal, intradermal, parenteral, intravenous, intramuscular and ocular systems, as well as traversing the blood-brain barrier.

Dosage unit forms can also include any one or combination of excipients, diluents, disintegrants, lubricants, plasticizers, colorants, flavorants, taste-masking agents, sugars, sweeteners, salts, and dosing vehicles, including, but not limited to, water, 1,2-propane diol, ethanol, olive oil, or any combination thereof.

The compounds and compositions of the subject invention are useful for administering biologically or chemically active agents to any animals, including but not limited to birds such as chickens; mammals, such as rodents, cows, pigs, dogs, cats, primates, and particularly humans; and insects.

The system is particularly advantageous for delivering chemically or biologically active agents that would otherwise be destroyed or rendered less effective by conditions encountered before the active agent reaches its target zone (i.e. the area in which the active agent of the delivery composition is to be released) and within the body of the animal to which they are administered. Particularly, the compounds and compositions of the present invention are useful for orally administering active agents, especially those that are not ordinarily orally deliverable, or those for which improved delivery is desired.

The compositions comprising the compounds and active agents have utility in the delivery of active agents to selected biological systems and in an increased or improved bio-availability of the active agent compared to administration of the active agent without the delivery agent. Delivery can be improved by delivering more active agent over a period of time, or in delivering the active agent in a particular time period (such as to effect quicker or delayed delivery), or in delivering the active agent at a specific time, or over a period of time (such as sustained delivery).

Another embodiment of the present invention is a method for the treatment or prevention of a disease or for achieving a desired physiological effect, such as those listed in the table below, in an animal by administering the composition of the present invention. Preferably, an effective amount of the composition for the treatment or prevention of the desired disease or for achieving the desired physiological effect is administered. Specific indications for active agents can be found in the Physicians' Desk Reference (54$^{th}$ Ed., 2000, Medical Economics Company, Inc., Montvale, N.J.) and (58$^{th}$ Ed. 2004, Medical Economics Company, Inc., Montvale N.J.), which are herein incorporated by reference. Specific indications for active agents can also be found in Fauci, A S, et. al., Harrison's Principles of Internal Medicine (14$^{th}$ Ed., 1998, McGraw-Hill Health Professions Division, New York. The active agents in the table below include their analogs, fragments, mimetics, and polyethylene glycol-modified derivatives, and can be administered with HPOD to improve the bio-availability of the active agent, as compared to administering the active agent alone.

| Active Agent | Disease and Physiological Effect |
|---|---|
| Amylin and Amylin Agonists; | Obesity |
| Adrenocorticotropin; | High Cholesterol (To Lower Cholesterol) |
| Antigens; | Infection |
| Antimicrobials, including Antibiotics, Anti-Bacterials and Anti-Fungal Agents; non-limiting examples of Antibiotics include Gram- | Infection Including Gram-Positive Bacterial Infection |

-continued

| Active Agent | Disease and Physiological Effect |
|---|---|
| Positive Acting, Bacteriocidal, Lipopeptidal and Cyclic Peptidal Antibiotics, such as Daptomycin And Analogs thereof; | |
| Anti-Migraine Agents such as BIBM-4096BS And Other Calcitonin Gene-Related Proteins Antagonists, Sumatriptan Succinate; | Migraines |
| Antivirals including Acyclovir, Valacyclovir; | Viral Infections |
| Atrial Naturetic Factor; | Vasodilation |
| Argatroban | Prophylaxis and treatment of thrombosis in patients with herapin-induced throbocytopenia ("HIT"), as well as an anticoagulant therapy in patients who have or are at risk for HIT undergoing percutaneous coronary intervention ("PCI"). Argatroban is also useful to treat thrombotic and isechemic stroke. |
| Bisphosphonates, including Alendronate, Clodronate, Etidronate, Ibandronate, Incadronate, Minodronate, Neridronate, Olpadronate, Pamidronate, Risedronate, Tiludronate, Zoledronate, EB1053, and YH529; | Osteoporosis; Paget's disease; Inhibits osteoclasts and Promotes osteoblastic activity; treat and/or prevent bone mineral density (bmd) loss; Breast cancer, including as adjuvant therapy for early stage breast cancer; Prostate cancer,; Testicular cancer; Colon cancer; Pancreatic cancer; Endometrial cancer; Small cell and non-small cell cancer of the lung; Ovarian cancer; Cervical cancer; Myeloid leukemia,; Lymphocyltic leukemia; Lymphoma; Hepatic tumors; Medullary thyroid carcinoma; Multiple myeloma; Melanoma retinoblastoma; Sarcomas of the soft tissue and bone; Hypercalcemia including hypercalcemia associated with malignancy; Osteolytic bone metastases and bone tumors; prevention of bone complications related to malignant osteolysis; Osteolytic lesions of multiple myeloma, fibrous dysplasia; pediatric osteogenesis imperfecta; hypercalcemia, urethral (urinary tract) malignancies, reflex sympathetic dystropy synodrome, acute back pain after vertebral crush fracture, chronic inflammatory joint disease, renal bone disease, extrosseous calcifications, analgesic, vitamin D intoxication, periarticular ossifications |
| BIBN4096BS - (1-Piperidinecarboxamide. N-[2-[[5-amino-1-[[4-(4-pyridinyl)-1-piperazinyl)carbonyl]pentyl]amino]-1-[(3,5-dibromo-4-hydroxyphenyl)methyl]-2-oxoethyl]-4(1,4-dihydro-2-oxo-3(2H0-quinazolinyl)-.[R-(R*,S*)]-) | Anti-migraine; calcitonin gene-related peptide antagonist |
| Calcitonin, including Salmon, Eel, Porcine And Human; | Osteoporosis; diseases of the bone; bone pain; analgesic (including pain associated with osteoporosis or cancer) |
| Cholecystokinin (CCK) And CCK Agonists Including CCK-8; | Obesity |
| Cromolyn Sodium (Sodium Or Disodium Chromoglycate); | Asthma; Allergies |
| CPHPC | Reduction of amyloid deposits and systemic amyloidoisis often (but not always) in connection with Alzheimer's disease, Type II diabetes, and other amyloid-based diseases |
| Cyclosporine; | Transplant Rejection |
| Desferrioxamine (DFO); | Iron Overload |
| Erythropoietin; | Anemia |
| Exedin and Exedin Agonists, including Exendin-3, Exendin-4; | Diabetes; Obesity |
| Filgrastim | Reduce Infection In Chemotherapy Patients |
| Follicle Stimulating Hormone (recombinant and natural); | Regulate Reproductive Function |
| Gallium nitrate | Osteoporosis; Paget's disease; Inhibits osteoclasts; Promotes osteoblastic activity, hypercalcemia, including cancer related hypercalcemia, urethral (urinary tract) malignancies; anti-tumors, cancers, including urethral and bladder cancers; lymphoma; malignancies (including bladder cancer); leukemia; management of bone metastases (and associated pain); muliple myeloma, attenuate immune response, including allogenic transplant rejections; disrupt iron metabolism; promote |

-continued

| Active Agent | Disease and Physiological Effect |
| --- | --- |
| | cell migration; wound repair; to attenuate or treat infectious processes of *mycobacterium* species, including but not limited to *mycobacterium tubercolosis*, and *mycobacterium avium* complex |
| Glucagon | improving glycemic control (e.g. treating hypoglycemia and controlling hypoglycemic reactions), obesity; a diagnostic aid in the radiogical examination of the stomach, duodenum, small bowel and colon; Treat acute poisoning With Cardiovascular Agents including, but not limited to, calcium channel blockers, beta blockers |
| Glucagon-Like Peptide 1 (GLP-1), Glucagon, and Glucagon-Like Peptide 2 (GLP-2); | Diabetes; Obesity |
| Glucocerebrosidase; | Gaucher Disease (To Metabolize Lipoprotein) |
| Gonadotropin Releasing Hormone; | Ovulatory Disfunction (To Stimulate Ovulation) |
| Growth Hormone Releasing Factor; | Growth Disorders |
| Growth Hormone Releasing Hormones; | Growth Disorders |
| Growth Hormones, Including Human Growth Hormones (hGH), Recombinant Human Growth Hormones (rhGH), Bovine Growth Hormones, And Porcine Growth Hormones; | Growth Disorders |
| Heparin, Including Unfractionated Heparin, Heparinoids, Dermatans, Chondroitins, Low Molecular Weight Heparin, Very Low Molecular Weight Heparin Ultra Low Molecular Weight Heparin and synthetic heparins including Fondiparinux; | Thrombosis; Prevention Of Blood Coagulation |
| Insulin, Including Porcine, Bovine, Human, And Human Recombinant, Optionally Having Counter Ions Including Zinc, Sodium, Calcium And Ammonium; | Diabetes; Insulin Resistance Syndrome |
| Insulin-Like Growth Factor, Including IGF-1; | Diabetes |
| Interferons, Including α (E.G., Interferon Alfacon-1 (Available As Infergen ® From Intermune, Inc. Of Brisbane, Ca)), alpha, β, OMEGA and γ; | Viral Infection, Including Chronic Cancer And Multiple Sclerosis |
| Interleukin-1; Interleukin-2; Interleukin-11; Interleukin-21; | Viral Infection; Cancer |
| Leutinizing Hormone and Leutinizing Hormone Releasing Hormone; | Regulate Reproductive Function |
| Leptin (OB Protein); | Obesity |
| Methyphenidate salt | ADHD, Attention Deficit Disorder, Dementia, AIDS Dementia Complex, cognitive decline in HIV-AIDS |
| Monoclonal Antibodies including Retuxin, TNF-alpha soluble receptors; | To Prevent Graft Rejection; Cancer |
| Oxytocin; | Labor Dysfunction (To Stimulate Contractions) |
| Parathyroid Hormone (PTH), Including Its Fragments, including PTH 1–34 and PTH 1–38; | Osteoporosis; Diseases Of The Bone |
| Peptide YY (PYY) Including PYY Agonists, Fragment 3–36; | Obesity; Diabetes; Eating Disorders; Insulin Resistance Syndrome |
| dipeptidyl peptidase IV (DPP-4) inhibitors | Diabetes; improving glycemic control (e.g. treating hypoglycemia), obesity |
| Prostaglandins; | Hypertension |
| Protease Inhibitors; | AIDS |
| Somatostatin; | Bleeding ulcer; erosive gastritis; variceal bleeding; diarrhea; acromegaly; TSH-secreting pituitary adenomas; secretory pancreatic tumors; carcinoid syndrome; reduce proptosis/thyroid-associated ophthalmopathy; reduce macular edema/retinopathy |
| Thrombopoietin; | Thrombocytopenia |
| Vancomycin; | Treat or prevent antimicrobial-induced infections including, but not limitted to methacillin-resistant *Staphalococcus aureus* and *Staph. epidermiditis* |
| Vitamins | Vitamin deficiencies |
| Vaccines Including Those Against Anthrax Or *Y. Pestis*, Influenza, and Herpes; | Prevent And Minimize Disease |

For example, one embodiment of the present invention is a method for treating a patient having or susceptible to diabetes by administering insulin and at least one of the delivery agent compounds of the present invention. Other active agents, including those set forth by way of non-limiting example in the above table, can be used in conjunction with the delivery agents of the present invention.

Following administration, the active agent present in the composition or dosage unit form is taken up into the circulation. The bioavailability of the agent can be readily assessed by measuring a known pharmacological activity in blood, e.g. an increase in blood clotting time caused by heparin, or a decrease in circulating calcium levels caused by calcitonin. Alternately, the circulating levels of the active agent itself can be measured directly.

One embodiment of the present invention is a method for treating an animal (e.g., a person (man or woman) or other mammal) in need thereof suffering from osteoporosis, (e.g., osteoporosis in postmenopausal women) by administering an effective amount of a pharmaceutical composition comprising one or more delivery agent compounds of the present invention and one or more bisphosphonates. Preferably, the bisphosphonate containing pharmaceutical composition is administered orally. Examples of suitable bisphosphonates include, but are not limited to alendronate, clodronate, etidronate, ibandronate, incadronate, minodronate, neridronate, olpadronate, pamidronate, risedronate, tiludronate, zoledronate, EB1053, and YH529. A preferred bisphosphonate is ibandronate.

According to one embodiment, the daily dose of bisphosphonate for the treatment of osteoporosis ranges from about 0.5 mg to about 50 mg per day in single or divided doses. According to another embodiment, the daily dose for the treatment of osteoporosis ranges from about 1 mg to about 20 mg/day or from about 2.5 mg to 10 mg/day.

Another embodiment is a method for treating an animal (e.g., a person (man or woman) or other mammal) in need thereof suffering from a malignant disease such as breast, prostate, testicular or colon cancer, or other neoplasms, such as pancreatic cancer, endometrial cancer, small cell and non-small cell cancer of the lung (including squamous, adneocarcinoma and large cell types), squamous cell of the head and neck, bladder, ovarian and cervical cancers, myeloid and lymphocyltic leukemia, lymphoma, hepatic tumors, medullary thyroid carcinoma, multiple myeloma, melanoma retinoblastoma, and sarcomas of the soft tissue and bone, i.e. neoplasms that express vitamin D receptors, by administering an effective amount of the aforementioned bisphosphonate containing pharmaceutical composition. For example, the bisphosphonate containing pharmaceutical composition can be administered to treat a malignant disease, such as breast or prostate cancer.

Yet another embodiment is a method for treating hypercalcemia of malignancy ("HCM"), including either osteolytic HCM (HCM with bone metastases) or humoral HCM (HCM without skeletal involvement) in an animal (e.g., a person (man or woman) or other mammal) in need thereof by administering an effective amount of the aforementioned bisphosphonate containing pharmaceutical composition to a patient in need thereof. For example, the bisphosphonate containing pharmaceutical composition can be administered to treat HCM in a patient having breast or prostate cancer.

Yet another embodiment is a method for treating osteolytic bone metastases in an animal (e.g., a person (man or woman) or other mammal) in need thereof, by administering an effective amount of the aforementioned bisphosphonate containing pharmaceutical composition. For example, the bisphosphonate containing pharmaceutical composition can be administered to treat osteolyitc bone metastases in a patient having breast or prostate cancer.

Yet another embodiment is a method for treating multiple myeloma in an animal (e.g., a person (man or woman) or other mammal) in need thereof, by administering an effective amount of the aforementioned bisphosphonate containing pharmaceutical composition.

Yet another embodiment is a method for treating osteolytic lesions in an animal (e.g., a person (man or woman) or other mammal) suffering from multiple myeloma by administering an effective amount of the aforementioned bisphosphonate containing pharmaceutical composition. For example, the bisphosphonate containing pharmaceutical compositions may be administered to decrease the incidents of osteolytic lesions associated with multiple myeloma, thereby reducing patient pain and the occurrence of spontaneous fractures.

The amount of bisphosphonate to be used for the treatment of any one of the diseases and/or physiological effects discussed above, can be determined by methods known to those skilled in the art. However, because the compositions of the invention may deliver bisphosphonates more efficiently than compositions without the delivery agent compound of the present invention, lower amounts of bisphosphonate than those used in prior dosage unit forms or delivery systems can be administered to the subject, while still achieving the same blood levels and/or therapeutic effects.

According to one embodiment, the daily dose of bisphosphonate for the treatment of any of the aforementioned malignant diseases or for a condition associated with the same (e.g., hypercalcemia of malignancy and osteolytic bone metastases) ranges from about 1 mg to about 100 mg per day in single or divided doses. According to another embodiment, the daily dose of bisphosphonate ranges from about 5 mg to about 75 mg/day, and more preferably from about 10 mg to 50 mg/day.

In all the methods described above, the bisphosphonate containing pharmaceutical composition is preferably administered orally.

Pharmaceutical Compositions

The pharmaceutical composition is preferably in solid form and may be formed into a solid dosage form. The solid dosage form can be a capsule, tablet or particle, such as a powder or sachet. The powder may be in the form of a sachet that is mixed with a liquid and administered. The solid dosage form may also be a topical delivery system, such as an ointment, cream or semi-solid. The solid dosage form contemplated may include a sustained release or controlled release system. Preferably, the solid dosage form is for oral administration.

The powder may be packed into capsules, or pressed into tablets, used in powder form, or incorporated into an ointment, cream or semi-solid. Methods for forming solid dosage forms are well known in the art.

The amount of delivery agent in the solid dosage form is a delivery effective amount and can be determined for any particular compound or biologically or chemically active agent by methods known to those skilled in the art. In one embodiment, the weight ratio of HPOD:active ranges from about 1:5 or 5:1 to about 300:1. More specifically, the ratio of HPOD:active may range from about 10:1 to about 200:1, or 50:1 to about 150:1. The amount of HPOD used will vary according to the active agent, and the particular indication for which the active agent is administered.

For embodiments in which the active agent is ibandronate, the ratio of HPOD:ibandronate may range from about 5:1 to about 300:1, or from about 10:1 to about 200:1, or 50:1 to about 150:1.

Following administration, the active agent in the dosage unit form is taken up into circulation. The bioavailability of the active agent is readily assessed by measuring a known pharmacological activity in blood, e.g. an increase in blood clotting time caused by heparin, or a decrease in circulating calcium levels caused by calcitonin. Alternately, the circulating levels of the active agent itself can be measured directly.

The solid dosage form may include pharmaceutically acceptable additives, such as excipients, carriers, diluents, stabilizers, plasticizers, binders, glidants, disintegrants, bulking agents, lubricants, plasticizers, colorants, film formers, flavoring agents, preservatives, dosing vehicles, surfactants, and any combination of any of the foregoing. Preferably, these additives are pharmaceutically acceptable additives, such as those described in *Remington's The Science and Practice of Pharmacy*, (Gennaro, A. R., ed., 19th edition, 1995, Mack Pub. Co.) which is herein incorporated by reference.

Suitable binders include, but are not limited to, starch, gelatine, sugars (such as sucrose, molasses and lactose), dibasic calcium phosphate dihydrate, natural and synthetic gums (such as acacia, sodium alginate, carboxymethyl cellulose, methyl cellulose, polyvinylpyrrolidone, polyethylene glycol, ethylcellulose, and waxes.

Suitable glidants include, but are not limited to, talc, and silicon dioxide (silica) (e.g, fumed silica and colloidal silicon dioxide).

Suitable disintegrants include, but are not limited to, starches, sodium starch glycolate, croscarmellose sodium, crospovidone, clays, celluloses (such as purified cellulose, methylcellulose, sodium carboxymethyl cellulose), alginates, pregelatinized corn starches, and gums (such as agar, guar, locust bean, karaya, pectin and tragacanth gums). A preferred disintegrant is sodium starch glycolate.

Suitable bulking agents include, but are not limited to, starches (such as rice starch), microcrystalline cellulose, lactose (e.g., lactose monohydrate), sucrose, dextrose, mannitol, calcium sulfate, dicalcium sulfate, and tricalcium sulfate.

Suitable lubricants include, but are not limited to, stearic acid, stearates (such as calcium stearate and magnesium stearate), talc, boric acid, sodium benzoate, sodium acetate, sodium fumarate, sodium chloride, polyethylene glycol, hydrogenated cottonseed, and castor oils.

Suitable surfactants include, but are not limited to, sodium lauryl sulfate, hydroxylated soy lecithin, polysorbates, and block copolymers of propylene oxide and ethylene oxide.

DESCRIPTION OF THE PREFERRED EMBODIMENTS

The following examples illustrate the invention without limitation. All parts are given by weight unless otherwise indicated.

Proton nuclear magnetic resonance ($^1$H NMR) analyses for the compounds listed below were conducted on a 300 MHz Bruker spectrometer using dimethyl sulfoxide (DMSO-$d_6$) as the solvent unless otherwise indicated.

EXAMPLE 1

Preparation of Compounds

1a: Preparation of the free acid of 8-(2-hydroxyphenoxy)octyldiethanolamine)

The free acid of HPOD was prepared as follows. The free acid of HPOD (i.e. 8-(2-hydroxyphenoxy)octyldiethanolamine) was prepared by the method described in Example 1 of International Publication No. WO 00/59863, which is hereby incorporated by reference in its entirety, using the appropriate starting materials.

The free acid of was prepared by preparing a solution of 27.5 ml (31.4 g, 157 mmol) of 2-benzyloxyphenol, 80.0 ml (118.82 g, 434 mmol) of 1,8-dibromooctane and 100 ml of ethanol was treated with 23.18 g (168 mmol) of potassium carbonate and heated to reflux for 5.5 hours. The cooled reaction mixture was stirred for 20 hours at 25° C., filtered and concentrated. The residue was diluted with 100 ml of 2:1 hexanes/ethyl acetate and decolorized with charcoal. The solution was concentrated. This residue was purified by Kugelrohr distillation to remove the excess dibromide at 98° C. and 0.5 mm of pressure.

The bromide isolated above (4.32 g, 11.0 mmol) and 2.80 ml (3.07 g, 29.2 mmol) of diethanolamine were dissolved in 30 ml of tetrahydrofuran and treated with 5 mL of triethylamine. This solution was heated to reflux for 3 days. The resulting slurry was cooled to 25° C., stirred at 25° C. for 20 hours and treated with 20 ml of 2N aqueous sodium hydroxide. This mixture was diluted with 20 ml of ethyl acetate. The layers were separated. The organic phase was washed with water (3×30 ml) and brine (1×30 ml), dried over sodium sulfate, and concentrated.

The 3.98 g of benzyl ether isolated above was dissolved in 20 ml of ethanol and 20 ml of ethyl acetate, treated with 0.22 g of 10% palladium on charcoal and placed under 58 psig of hydrogen in a Parr shaker. Approximately 20 psig of hydrogen was used up over 20 hours. The catalyst was removed by filtration through a Celite pad. The filtrate was concentrated and placed under vacuum over 20 hours.

1b: Preparation of 8-(2-hydroxyphenoxy)octyldiethanolamine)mesylate

The free acid of HPOD (i.e. 8-(2-hydroxyphenoxy)octyldiethanolamine) was prepared by the method described in Example 1 of International Publication No. WO 00/59863, which is hereby incorporated by reference in its entirety, using the appropriate starting materials.

A solution of 27.5 ml (31.4 g, 157 mmol) of 2-benzyloxyphenol, 80.0 ml (118.82 g, 434 mmol) of 1,8-dibromooctane and 100 ml of ethanol was treated with 23.18 g (168 mmol) of potassium carbonate and heated to reflux for 5.5 hours. The cooled reaction mixture was stirred for 20 hours at 25° C., filtered and concentrated. The residue was diluted with 100 ml of 2:1 hexanes/ethyl acetate and decolorized with charcoal. The solution was concentrated. This residue was purified by Kugelrohr distillation to remove the excess dibromide at 98° C. and 0.5 mm of pressure.

The bromide isolated above (4.32 g, 11.0 mmol) and 2.80 ml (3.07 g, 29.2 mmol) of diethanolamine were dissolved in 30 ml of tetrahydrofuran and treated with 5 mL of triethylamine. This solution was heated to reflux for 3 days. The resulting slurry was cooled to 25° C., stirred at 25° C. for 20 hours and treated with 20 ml of 2N aqueous sodium hydroxide. This mixture was diluted with 20 ml of ethyl acetate.

The layers were separated. The organic phase was washed with water (3×30 ml) and brine (1×30 ml), dried over sodium sulfate, and concentrated.

The 3.98 g of benzyl ether isolated above was dissolved in 20 ml of ethanol and 20 ml of ethyl acetate, treated with 0.22 g of 10% palladium on charcoal and placed under 58 psig of hydrogen in a Parr shaker. Approximately 20 psig of hydrogen was used up over 20 hours. The catalyst was removed by filtration through a Celite pad. The filtrate was concentrated and placed under vacuum over 20 hours.

A solution of 8-(2-hydroxyphenoxy)octyldiethanolamine (13.38 g, 41.1 mmol, isolated as described above) and 40 ml of methyl t-butyl ether was treated with 2.60 mL (3.85 g, 40.1 mmol) of methane sulfonic acid. The resulting solid was isolated by filtration to give 14.00 g of 8-(2-hydroxyphenoxy)octyldiethanolammonium mesylate. Karl Fisher: 1.71% water; Combustion analysis (with water): % C, 53.21 (calc'd), 52.79 (found); % H, 8.42 (calc'd), 9.40 (found); % N, 3.27 (calc'd), 3.02 (found). $^1$H NMR Analysis: (d6-DMSO): δ 12.4, bs, 1H (COOH); δ 8.88, bs, 1H (ArOH); δ 6.82, dd, 1H (arylH); δ 6.71, td, 1H (arylH); δ 6.66, m, 2H (arylH); δ 4.88, bs, 2H(OH); δ 3.86, t, 2H, ($CH_2$ α to ArO); δ 3.68, t, 4H, ($CH_2$'s α to OH); δ 3.17, m, 4H, ($CH_2$'s α to N); δ 3.08, m, 2H, ($CH_2$ α to N); δ 2.27, s, 3H, $CH_3SO_3$); δ 1.62, m, 2H ($CH_2$ in chain); δ 1.25, m, 8H($CH_2$'s in chain). $^{13}$C NMR (d6-DMSO): 146.88, 146.84, 120.90, 119.12, 115.63, 113.75, 68.20, 55.19, 54.44, 53.06, 28.76, 28.56, 28.46, 25.91, 25.35, 22.77.

EXAMPLE 2

Oral Absorption of Ibandronate

Summary

Oral absorption studies were performed in rats to evaluate the delivery of the bisphosphonate, Ibandronate, when co-administered with a delivery agent compound of the present invention. Sprague-Dawley rats were administered Ibandronate alone or in combination with a delivery agent compound by oral gavage. Urine samples were collected up to 16 hours post-dosing for Ibandronate quantitations. The data show that substantially higher levels of Ibandronate were achieved via the oral route of administration following co-administration with the delivery agent compound of the present invention than when Ibandronate was administered orally alone. The formulation containing the mesylate salt of HPOD resulted in urine concentration levels of ibandronate 5.7 times higher and at a 5-fold lower dose than ibandronate alone.

Materials and Methods

Dosing and Dosing Solutions

Four delivery agents, monosodium N-[8-(2-hydroxybenzoyl)amino]caprylate ("SNAC"), 8-(5-fluorosalicyloyl)aminocaprylic acid ("FSAA"), 8-(2-hydroxyphenoxy)octyldiethanolamine) mesylate ("HPOD" mesylate), and monosodium N-(10-[2-hydroxybenzoyl]amino)decanoic acid ("SNAD") were screened to evaluate their ability to deliver Ibandronate in a single oral dose in male Sprague-Dawley rats (n=12/dose group). Animals were fasted overnight (16–24 hours). Food was returned to the animals 4 hours post-dosing for a duration of 2 hours. Water was provided ad libitum.

Dosing solutions were made fresh on the day of dosing. Carrier solutions were prepared in sterile water at a concentration of 200 mg/ml and pH-adjusted into solution at a range of 5.5–7.5. Ibandronate was supplied as a bulk powder from F. Hoffmann-La Roche (Nutley, N.J.). Ibandronate was prepared in phosphate-buffered saline (pH 7.4) at a stock concentration of 5 or 15 mg/ml and added to the appropriate carrier solution prior to administration. The dose volume for the Ibandronate alone and Ibandronate/delivery agent solutions was 1 ml/kg.

Each half of a group was dosed subsequently with two different doses using a cross-over design. On Day 1, six rats per group were treated with the lower dose and the other six rats received the higher dose. After a washout period of 3 days, the six rats previously treated with the low dose then received the high dose and the previously high dosed animals then received the low dose. After each dosing, animals were housed in metabolism cages for 16 hours for urine collection. The dosing regime is summarized in Table 1, below.

TABLE 1

| Group No. | Delivery Agent | Ibandronate Dose Level (mg/kg) | Delivery Agent Level (mg/kg) |
|---|---|---|---|
| 1 | none | 5 and 15 | 0 |
| 2 | SNAC | 1 and 3 | 200 |
| 3 | FSAA | 1 and 3 | 200 |
| 4 | HPOD mesylate | 1 and 3 | 200 |
| 5 | SNAD | 1 and 3 | 200 |

Sample Collection

Urine was collected for 16 hours post-dosing from animals housed in metabolism cages. Specimen containers were kept on wet ice for the duration of the collection. Following the collection period, urine samples were stored at −20° C.

Bioanalytical Methods

Urine Ibandronate levels from treated rats were determined using a GC/MS method with a standard calibration range of 0–2000 ng/mL and a limit of quantitation (LOQ) of 2.5 ng/ml. Quality control (QC) samples were prepared fresh daily and were analyzed with samples from treated rats. The concentrations of QC samples were 7.5, 400, and 1600 ng/mL.

Statistical Analysis

The amount of Ibandronate excreted in the urine is the dose response and was plotted as a straight line against the Ibandronate dose (linear dose-response relationship was assumed). The relative potency of the four delivery agent-containing Ibandronate formulations were calculated against the control formulations (without delivery agent) using a Student's t-test.

Results and Discussion

Figure 2:
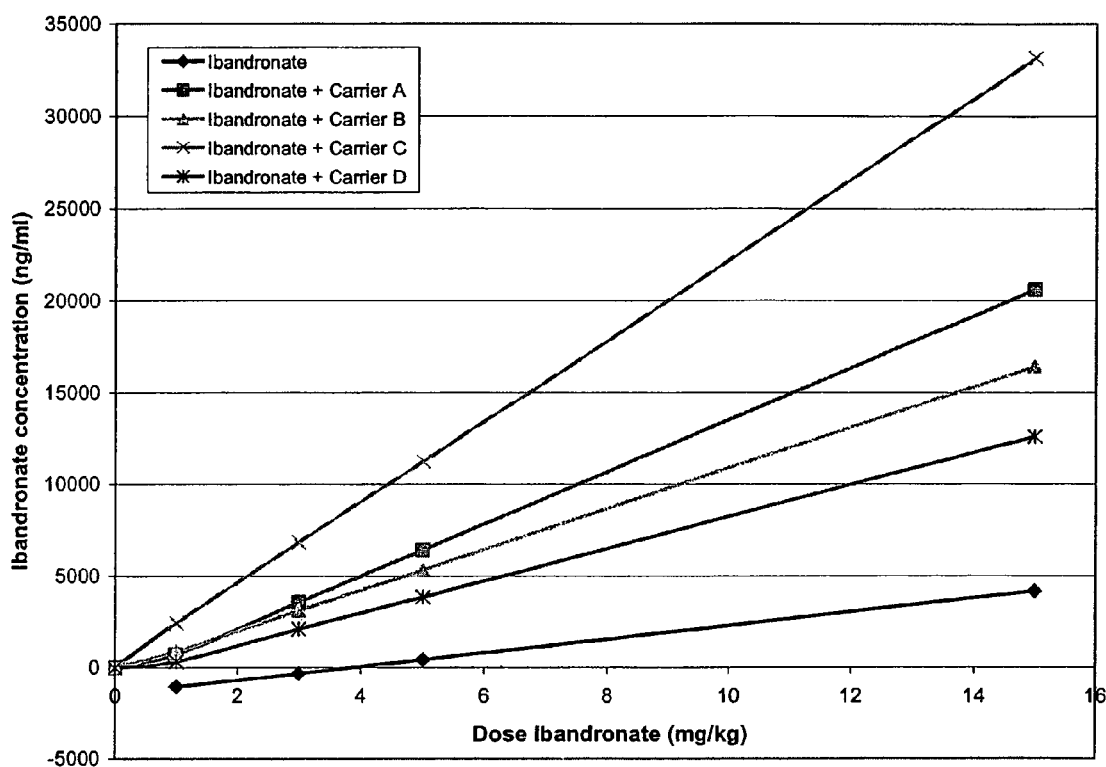
FIG. 2 depicts the predicted Ibandronate concentration following administration of Ibandronate alone (-♦-) or with any one of four delivery agents (SNAC (-■-), FSAA (-▲-), HPOD mesylate (-x-), and SNAD (-*-))

Mean urine Ibandronate concentration data are shown in FIG. 1. The results are also summarized in Tables 2 below. FIG. 2 reflects the predicted urine Ibandronate concentrations after treatment with Ibandronate or Ibandronate/delivery agent, assuming a linear dose-response. The data plotted in FIG. 2 are extrapolated from the mean data presented in FIG. 1.

TABLE 2

Statistically significant (p ≦ 0.05) finding of the present example

| Treatment group | Mean | p-value (p ≦ 0.05) vs. Ibandronate (5 mg/kg) | Fold increase | p-value vs. Ibandronate (15 mg/kg) | Fold increase |
|---|---|---|---|---|---|
| Ibandronate (5 mg/kg) | 426.8 | — | | — | |
| Ibandronate (15 mg/kg) | 4157.5 | — | | — | |
| SNAC + Ibandronate (1 mg/kg) | 730.7 | 0.068 | 1.7 | Iban> | — |
| SNAC + Ibandronate (3 mg/kg) | 3566.7 | 0.0002* | 8.4 | NS | — |
| FSAA + Ibandronate (1 mg/kg) | 894.7 | 0.065 | 2.1 | Iban> | — |
| FSAA + Ibandronate (3 mg/kg) | 3113.8 | 0.001* | 7.3 | NS | — |
| HPOD mesylate + Ibandronate (1 mg/kg) | 2451.3 | 0.005* | 5.7 | NS | — |
| HPOD mesylate + Ibandronate (3 mg/kg) | 6837.5 | 0.000002* | 16 | 0.039* | 1.6 |
| SNAD + Ibandronate (1 mg/kg) | 353.5 | NS | — | Iban> | — |
| SNAD + Ibandronate (3 mg/kg) | 2101.5 | 0.006* | 4.9 | Iban> | — |

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

Patents, patent applications, publications, product descriptions, and protocols are cited throughout this application, the disclosures of which are incorporated herein by reference in their entireties for all purposes.

What is claimed is:

1. A method for treating a malignant disease in a person in need thereof comprising administering an effective amount of a pharmaceutical composition comprising (a) at least one compound selected from 8-(2-hydroxyphenoxy) octyldiethanolamine and salts thereof, and (b) one more bisphosphonates to the person, wherein the malignant disease is selected from breast cancer, prostate cancer, testicular cancer, colon cancer, pancreatic cancer, endometrial cancer, small cell and non-small cell cancer of the lung, ovarian cancer, cervical cancer, myeloid leukemia, lymphocyltic leukemia, lymphoma, hepatic tumors, medullary thyroid carcinoma, multiple myeloma, melanoma retinoblastoma, and sarcomas of the soft tissue and bone.

2. The method claim 1, wherein the compound in component (a) is a mesylate salt of a 8-(2-hydroxyphenoxy) octyldiethanolamine.

3. The method of claim 2, wherein the bisphosphonate is selected from alendronate, clodronate, etidronate, ibandronate, incadronate, minodronate, neridronate, olpadronate, pamidronate, risedronate, tiludronate, zoledronate, EB1053, YH529, or a mixture thereof.

4. The method of claim 2, wherein the bisphosphonate is ibandronate.

5. The method of claim 1, wherein the malignant disease is breast or prostate cancer.

6. A method for treating hypercalcemia of malignancy in a person in need thereof, comprising administering an effective amount of a pharmaceutical composition comprising (a) at least one compound selected from 8-(2-hydroxyphenoxy) octyldiethanolamine and salts thereof, and (b) one more bisphosphonates to the person.

7. The method claim 6, wherein the compound in component (a) is a mesylate salt of a 8-(2-hydroxyphenoxy) octyldiethanolamine.

8. The method of claim 7, wherein the bisphosphonate is selected from alendronate, clodronate, etidronate, ibandronate, incadronate, minodronate, neridronate, olpadronate, pamidronate, risedronate, tiludronate, zoledronate, EB1053, YH529, or a mixture thereof.

9. The method of claim 7, wherein the bisphosphonate is ibandronate.

10. A method for treating osteolytic bone mestastases in a person in need thereof, comprising administering an effective amount of a pharmaceutical composition comprising (a) at least one compound selected from 8-(2-hydroxyphenoxy) octyldiethanolamine and salts thereof, and (b) one more bisphosphonates to the person.

11. The method claim 10, wherein the compound in component (a) is a mesylate salt of a 8-(2-hydroxyphenoxy) octyldiethanolamine.

12. The method of claim 11, wherein the bisphosphonate is selected from alendronate, clodronate, etidronate, ibandronate, incadronate, minodronate, neridronate, olpadronate, pamidronate, risedronate, tiludronate, zoledronate, EB1053, YH529, or a mixture thereof.

13. The method of claim 11, wherein the bisphosphonate is ibandronate.

14. The mesylate salt of

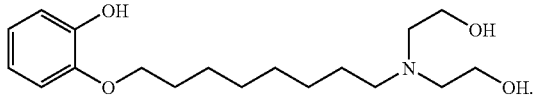

15. A composition comprising:
(a) an active agent; and
(b) the mesylate salt of claim 14.

16. The composition of claim 15, wherein the active agent is a bisphosphonate.

17. The composition of claim 16, wherein the bisphosphonate is selected from alendronate, clodronate, etidronate, ibandronate, incadronate, minodronate, neridronate, olpadronate, pamidronate, risedronate, tiludronate, zoledronate, EB1053, YH529, or a mixture thereof.

18. A method of administering an active agent comprising administering the composition of claim 15.

19. A method of administering a bisphosphonate comprising administering the composition of claim 16.

20. The method of claim 2, wherein the bisphosphonate is alendronate.

21. The method of claim 7, wherein the bisphosphonate is alendronate.

22. The method of claim 11, wherein the bisphosphonate is alendronate.

23. The composition of claim 16, wherein the bisphosphonate is alendronate.

24. The method of claim of claim 19, wherein the bisphosphonate is alendronate.

* * * * *